(12) United States Patent
Hojo et al.

(10) Patent No.: US 7,785,705 B2
(45) Date of Patent: Aug. 31, 2010

(54) FLOWER THINNING AGENT

(75) Inventors: Hisakazu Hojo, Hyogo (JP); Hiroshi Shibata, Hyogo (JP); Naoki Kubota, Hyogo (JP); Nariatsu Uto, Hyogo (JP); Toshio Fujiwara, Hyogo (JP)

(73) Assignee: Maruo Calcium Company Limited, Akashi-Shi (JP)

( * ) Notice: Subject to any disclaimer, the term of this patent is extended or adjusted under 35 U.S.C. 154(b) by 162 days.

(21) Appl. No.: 10/523,034

(22) PCT Filed: Aug. 1, 2003

(86) PCT No.: PCT/JP03/09797

§ 371 (c)(1),
(2), (4) Date: Feb. 2, 2005

(87) PCT Pub. No.: WO2004/012507

PCT Pub. Date: Feb. 12, 2004

(65) Prior Publication Data

US 2005/0245396 A1 Nov. 3, 2005

(30) Foreign Application Priority Data

Aug. 2, 2002 (JP) .............................. 2002-225712

(51) Int. Cl.
*B32B 5/16* (2006.01)
(52) U.S. Cl. .................. 428/332; 504/367; 428/402
(58) Field of Classification Search .......... 428/198, 428/402, 322; 504/367
See application file for complete search history.

(56) References Cited

U.S. PATENT DOCUMENTS

| | | | | |
|---|---|---|---|---|
| 4,844,734 A | * | 7/1989 | Iwasaki et al. ............... | 504/330 |
| 4,931,080 A | * | 6/1990 | Chan et al. .................. | 504/206 |
| 5,252,118 A | * | 10/1993 | Brown .......................... | 71/23 |
| 6,110,866 A | * | 8/2000 | Walker ........................ | 504/118 |
| 6,936,681 B1 | * | 8/2005 | Wertz et al. ................. | 528/259 |
| 2001/0042494 A1 | * | 11/2001 | Welshimer et al. .......... | 106/772 |

FOREIGN PATENT DOCUMENTS

| | | |
|---|---|---|
| EP | 870435 A1 * | 10/1998 |
| JP | 55-13233 | 1/1980 |
| JP | 55-013233 | 1/1980 |
| JP | 58-157706 | 9/1983 |
| JP | 07-118108 | 5/1995 |
| JP | 7-118108 | 5/1995 |
| JP | 09-302327 | 11/1997 |

OTHER PUBLICATIONS

US Mesh vs Micron conversion table, 1998.*
International Search Report dated Dec. 9, 2003.

* cited by examiner

*Primary Examiner*—Elizabeth M Cole
(74) *Attorney, Agent, or Firm*—Kratz, Quintos & Hanson, LLP

(57) ABSTRACT

The flower thinning agent of the present invention comprises a preparation of a mixture of an inorganic compound of poor water solubility with an additive, satisfying the following relationships of (a) $0.03 \leq P \leq 30$, (b) $3 \leq Q \leq 800$, and (c) $0.5 \leq Q/P \leq 1000$, wherein P: average particle diameter (μm) measured by SALD-2000A laser type particle size distribution meter, Q: BET specific surface area ($m^2/g$) measured according to the nitrogen adsorption method. The flower thinning agent of the present invention is not harmful to a human body and has not only high adaptability to the deflection of spread timing, but also high flower thinning effect.

8 Claims, No Drawings ly, a flower

FLOWER THINNING AGENT

This application is a national stage entry of PCT/JP03/09797 filed Aug. 1, 2003.

TECHNICAL FIELD

The present invention relates to a flower thinning agent, more particularly, a flower thinning agent useful for apple, pear, peach, grape and persimmon, which has no adverse effect on the environment, gives little possibility of medicine damage, and hardly undergoes influence of a district, weather and the like.

BACKGROUND ART

Among work of fruit tree cultivating farmhouses, work of picking a bud, picking a flower, and picking a fruit for limiting the number of born fruits, and picking leaves aimed at uniform coloring of fruits are a considerably great burden. For example, in an apple, it is said that a ratio of these works occupied in all work accounts for about a half. Among them, work of picking a bud, picking a flower and picking a fruit is important work greatly acting on fruit quality, but since it is necessary that the work is finished in a predetermined short term, a burden on fruit tree farmhouses is great and, in particular in Japan, there is also a problem of aging in an agricultural population, and labor saving is a great theme. These pickings, bud picking, flower picking and fruit picking, are accepted to be a necessary work not only in apple, but also pear, peach, grape, persimmon, citrus fruits, and the work restricts the number of fruits, promoting enlargement of a fruit and development of a branch leaf. Among them, flower picking is performed not only by a manual working method, scattering of a flower thinning agent has been practiced heretofore.

As a flower thinning agent which has been previously proposed and put into practice, for example, there is a flower thinning agent containing a lime and sulfur mixture as an effective ingredient. However, a lime and sulfur mixture has certain effect, but since it is strongly basic and, at the same time, has a strong offensive smell and may have adverse effect on a living body, workability is deteriorated and handling was problematic such as necessity of taking protecting means with a mask, protecting spectacles, or protecting robe. In addition, since a lime and sulfur mixture is strongly basic, there is a fear that a metal of a scattering equipment is eroded. In order to improve this phenomenon, when an amount of lime is decreased and a pH reaches a neutral region, there is a tendency that medicine damage phenomenon such as discoloration of a leaf becomes intense due to increase in an amount of sulfur, therefore, it is not a preferable method to adjust a pH. Further, in the case of use of the lime and sulfur mixture, when a flower visiting insect such as a honey bee and the like is activated, a bad smell based on sulfur is brought by a honey bee, there is a possibility that quality of a honey is deteriorated and, recently, this has become a problem. Therefore, it is hard to say that use of a lime and sulfur mixture is preferable in a respect of side effect although certain flower thinning effect is recognized.

In addition, in JP-A No. 2000-290103, JP-A No. 2001-206804, and JP-A No. 2001-206805, there is provided a flower thinning agent containing, as an effective ingredient, an organic acid such as organic water-soluble citric acid, gluconic acid, succinic acid, lactic acid, fumaric acid, malic acid, acetic acid, tartaric acid, propionic acid and the like, and an organic acid salt. However, when the aforementioned organic acid and organic acid salt are used, if they are scattered within 1 to a few hours after flowering, certain flower thinning effect is recognized, but since a flower thinning agent is used under natural circumstance, it is extremely difficult to usually spread at aimed timing depending on a difference in a district, a change in weather and air temperature. When spread timing is deflected, since the effect is remarkably decreased, there is a defect that it is difficult to achieve stable flower thinning effect.

Further, in JP-A No. 2000-198704, and JP-A No. 2001-328910, there is provided a flower thinning agent containing an aliphatic organic acid such as itaconic acid and the like as an effective ingredient. However, when a medicine containing an aliphatic organic acid such as itaconic acid as an effective ingredient is used, although certain flower thinning effect is recognized, there is a problem that epinasty phenomenon where a leaf is curled or transiently hung and medicine damage such as browning of a leaf occur, thus, this use can not be said to be so preferable.

In addition, since all of the aforementioned substances are water-soluble substances, a flower thinning agent is easily flown away and, when spread proper term is rainy, there is a problem that flower thinning effect is hardly expected.

In addition, in JP-A No. 55-13233, and JP-A No. 58-157706, there is provided a flower thinning agent containing lecithin, plant sterol and the like as an effective ingredient. However, when lecithin or the like is used alone, certain flower thinning effect is recognized, but since durability of effect is insufficient, it is difficult to obtain sufficient flower thinning effect. The reason is thought as follows: that is, since a tree is grown naturally, there is a difference in strength of tree health in each tree unit and each branch unit. Therefore, it is difficult to completely adjust flowering timing of a flower at a flowering season. For this reason, although effect is recognized in a particular branch, effect is hardly confirmed in another branch in some cases, and, as a result, it is presumed that, when a total of a treating section is averaged, it is difficult to necessarily obtain sufficient flower thinning effect. In addition, when a spread concentration is increased in order to compensate for insufficiency of flower thinning effect, there is a tendency that medicine damage such as browning of a leaf occurs, being not preferable. Further, when the substances are dissolved in water and the like, a flower thinning agent is easily flown away and, in the case where a spread proper term is rainy, there is a problem that flower thinning effect is hardly expected.

In view of such the conditions, the present inventors solve the aforementioned problems, and provide a flower thinning agent which is safe for human health, exhibits high adaptability to spread timing deflection and further exhibits high flower thinning efficiency.

DISCLOSURE OF THE INVENTION

Aspect 1 of the present invention is to provide a flower thinning agent which comprises a preparation of a mixture of an inorganic compound of poor water solubility with an additive, satisfying the following relationships of (a), (b) and (c):

$$0.03 \leq P \leq 30 \tag{a}$$

$$3 \leq Q \leq 800 \tag{b}$$

$$0.5 \leq Q/P \leq 1000 \tag{c}$$

P: average particle diameter (μm) measured by SALD-2000A laser type particle size distribution meter Q: BET specific surface area (m²/g) measured according to the nitrogen adsorption method Aspect 2 of the present invention is to provide a flower thinning agent which comprises a preparation of a mixture of an inorganic compound of poor water solubility with an additive, satisfying the following relationships (d), (e) and (f):

$$0.03 \leq P \leq 10 \quad (d)$$

$$7 \leq Q \leq 300 \quad (e)$$

$$0.5 \leq Q/P \leq 300 \quad (f)$$

P: average particle diameter (μm) measured by SALD-2000A laser type particle size distribution meter Q: BET specific surface area (m²/g) measured according to the nitrogen adsorption method Aspect 3 of the present invention is to provide a flower thinning agent which comprises a preparation of a mixture of an inorganic compound of poor water solubility with an additive, satisfying the following relationships (g), (h) and (i):

$$0.03 \leq P \leq 5 \quad (g)$$

$$10 \leq Q \leq 200 \quad (h)$$

$$1 \leq Q/P \leq 150 \quad (i)$$

P: average particle diameter (μm) measured by SALD-2000A laser type particle size distribution meter Q: BET specific surface area (m²/g) measured according to the nitrogen adsorption method Aspect 4 of the present invention is to provide a flower thinning agent according to any one of claims 1 to 3, which comprises a preparation of a mixture of an inorganic compound of poor water solubility with an additive, satisfying the following relationships of (j), (k) and (l):

$$0.5 \leq Dys \leq 10 \quad (j)$$

$$0.002 \leq Dxs \leq 10 \quad (k)$$

$$0.5 \leq Dys/Dxs \leq 300 \quad (l)$$

Dys: point (ml/g) when mercury penetration increment (Log Differential Intrusion) becomes maximum in a mercury penetration method Dxs: average pore diameter (μm) of Dys Dys/Dxs amount of average pore diameter Aspect 5 of the present invention is to provide a flower thinning agent according to any one of claims 1 to 4, wherein the inorganic compound of poor water solubility is at least one kind selected from silicate mineral, calcium carbonate, zeolite, magnesium carbonate, and magnesium phosphate.

Aspect 6 of the present invention is to provide a flower thinning agent according to any one of claims 1 to 4, wherein the inorganic compound of poor water solubility is at least one kind selected from silicate mineral, zeolite, and magnesium phosphate.

Aspect 7 of the present invention is to provide a flower thinning agent which comprises a preparation of a mixture of an inorganic compound of poor water solubility comprising calcium phosphate with an additive, satisfying the following relationships of (a), (e), (m) and (n):

$$0.03 \leq P \leq 30 \quad (a)$$

$$3 \leq Q \leq 300 \quad (e)$$

$$0.01 \leq R \leq 30 \quad (m)$$

$$0.5 \leq S \leq 300 \quad (n)$$

P: average particle diameter (μm) measured by SALD-2000A laser type particle size distribution meter Q: BET specific surface area (m²/g) measured according to the nitrogen adsorption method R: average particle diameter (μm) of particles measured by electron micrograph S: porosity S=BET specific surface area Q (m²/g) measured according to the nitrogen adsorption method/specific surface area Q1 (m²/g) calculated from average particle diameter R of particles measured by electron micrograph Aspect 8 of the present invention is to provide a flower thinning agent which comprises a preparation of a mixture of an inorganic compound of poor water solubility comprising calcium phosphate with an additive, satisfying the following relationships of (a), (e), (o) and (t):

$$0.03 \leq P \leq 30 \quad (a)$$

$$3 \leq Q \leq 300 \quad (e)$$

$$0.01 \leq R \leq 10 \quad (o)$$

$$0.5 \leq S \leq 100 \quad (t)$$

P: average particle diameter (μm) measured by SALD-2000A laser type particle size distribution meter Q: BET specific surface area (m²/g) measured according to the nitrogen adsorption method R: average particle diameter (μm) of particles measured by electron micrograph S: porosity S=BET specific surface area Q (m²/g) measured according to the nitrogen adsorption method/specific surface area Q1 (m²/g) calculated from average particle diameter R of particles measured by electron micrograph Aspect 9 of the present invention is to provide a flower thinning agent which comprises a preparation of a mixture of an inorganic compound of poor water solubility comprising calcium phosphate with an additive, satisfying the following relationships of (a), (e), (u) and (v):

$$0.03 \leq P \leq 30 \quad (a)$$

$$3 \leq Q \leq 300 \quad (e)$$

$$0.01 \leq R \leq 5 \quad (u)$$

$$0.5 \leq S \leq 10 \quad (v)$$

P: average particle diameter (μm) measured by SALD-2000A laser type particle size distribution meter Q: BET specific surface area (m²/g) measured according to the nitrogen adsorption method R: average particle diameter (μm) of particles measured by electron micrograph S: porosity S=BET specific surface area Q (m²/g) measured according to the nitrogen adsorption method/specific surface area Q1 (m²/g) calculated from average particle diameter R of particles measured by electron micrograph Aspect 10 of the present invention is to provide a flower thinning agent according to any one of claims 1 to 9, wherein the additive is at least one kind selected from condensed phosphoric acid and a salt thereof, lecithin, sterol, amino acid, and sucrose fatty acid ester.

Aspect 11 of the present invention is to provide a flower thinning agent according to any one of claims 1 to 10, wherein an amount of the additive is 0.005 to 200 parts by weight per 100 parts by weight of the inorganic compound of poor water solubility.

BEST MODE FOR CARRYING OUT THE INVENTION

The inorganic compound of poor water solubility used in the present invention is not particularly limited as far as it is an inorganic compound of poor water solubility which can satisfy the aforementioned relationships of (a), (b) and (c) when formulated into a preparation of a mixture with an additive, and examples include calcium carbonate, calcium phosphate, magnesium carbonate, magnesium phosphate, barium sulfate, silicate compound, and zeolite, and these may be used alone or in combination of two or more.

Among them, calcium phosphate, magnesium carbonate, magnesium phosphate, silicate mineral and zeolite are preferable in that they easily make a preparation having appropriate porosity or appropriate dispersibility. More preferable are calcium phosphate, magnesium phosphate, silicate mineral and zeolite and, inter alia, particularly preferable is calcium phosphate.

Porosity of calcium phosphate is calculated as BET specific surface area Q ($m^2$/g) measured according to the nitrogen adsorption method/specific surface area Q1 ($m^2$/g) calculated from average particle diameter R of particles measured by electron micrograph, and it is preferable to adjust so as to have appropriate porosity so that a flowering thinning agent is released at a constant concentration for a constant time.

Examples of calcium phosphate of the present invention include amorphous calcium phosphate (abbreviation: ACP, chemical formula: $Ca_3(PO_4)_2 \cdot nH_2O$), fluorine apatite (abbreviation: FAP, $Ca_{10}(PO_4)_6F_2$), chlorine apatite (abbreviation: CAP, $Ca_{10}(PO_4)_6Cl_2$), hydroxyapatite (abbreviation: HAP, $Ca_{10}(PO_4)_6OH_2$), octacalcium phosphate (abbreviation: OCP, chemical formula: $Ca_8H_2(PO_4)_6 \cdot 5H_2O$), and tricalcium phosphate (abbreviation: TCP, chemical formula: $Ca_3(PO_4)_2$), and these may be used alone or in combination of two, or more, or may be a composition of a mixture of calcium carbonate and calcium phosphate. A composition of a mixture of calcium carbonate and calcium phosphate can be synthesized by a process of Japanese Patent Application No. 7-196144 and the like.

Among them, from a viewpoint of possession of appropriate size, porosity and dispersibility, a mixture of amorphous calcium phosphate, tricalcium phosphate, hydroxyapatite, a mixture of calcium phosphate with calcium carbonate is preferable, inter alia, amorphous calcium phosphate is most preferable, and these can be prepared by a process described in WO97-3016, WO03-17786, and WO03-32752.

Examples of reaction condition will be shown below, but the present invention is not limited to them.

(Combining Condition 1)
  (i) Dilute aqueous phosphoric acid solution: 1 to 50% by weight
  (ii) Amount of phosphoric acid to be added: 1 to 70% by weight (per CaCO3)
  (iii) Circumferential rate of mixing stirring wing: 0.5 m/sec or higher
  (iv) Mixing time: 0.1 to 150 hours
  (v) Temperature of mixed system aqueous suspension: 0 to 80° C.
  (vi) pH of Mixed system: 5 to 9

(Aging Condition 1)
  (i) Circumferential rate of aging wing: 0.5 m/sec or higher
  (ii) Aging time : 0.1 to 100 hours
  (iii) Temperature of aging system aqueous suspension: 20 to 80° C.
  (iv) pH of Aging system aqueous suspension: 6 to 9

In the aforementioned reaction condition, in order to reduce an average particle diameter (μm) of a particle measured by a SALD-2000 A laser type particle size distribution meter, a circumferential rate of a mixing stirring wing may be increased, or a mixing time may be lengthened. In order to reduce a BET specific surface area ($m^2$/g) measured according to the nitrogen adsorption method, an amount of phosphoric acid to be added may be decreased. In addition, in order to reduce a size of a particle measured by an electron microscope, or increase porosity, stirring condition at a reaction may be intensified.

(Combining Condition 2)
  Water, calcium hydroxide, and an organic acid having a carboxyl group are mixed to prepare a precursor, and a phosphoric acid source and an alkali metal source are added to the precursor.

A preferable mole ratio of each component at preparation is as follows:

Polyvalent metal ion: organic acid ion having carboxyl group=0.8:1 to 200:1

Organic acid ion having carboxyl group: phosphoric acid ion=1:0.6 to 1:140

Organic acid ion having carboxyl group: alkali metal ion=1:0.01 to 1:8

(Aging Condition 2)
  Temperature of aging system aqueous suspension: 80 to 230° C.
  Aging time: 0.5 to 48 hours In the aforementioned reaction condition, in addition to reduce an average particle diameter (μm) of a particle measured by a SALD-2000A laser type particle size distribution meter, or reduce a BET specific surface area ($m^2$/g) measured according to the nitrogen adsorption method, the aging temperature may be elevated, or an aging time may be lengthened. In addition, also by increasing an amount of an alkali metal source to be added, it becomes possible to reduce a BET specific surface area ($m^2$/g) measured according to the nitrogen adsorption method.

Examples of calcium carbonate in the present invention include heavy calcium carbonate, light calcium carbonate, colloidal calcium carbonate, and porous calcium carbonate, and these may be used alone or in combination of two or more. Colloidal calcium carbonate and porous calcium carbonate are preferable in that they have an appropriate size and appropriate dispersibility. Porous calcium carbonate is more preferable in that it has appropriate porosity. The aforementioned preferable calcium carbonate can be prepared by a process described in Japanese Patent No.3058255.

Examples of reaction condition will be shown below, but the present invention is not limited to them.

(Reaction Condition)
  Lime milk concentration: 3.5 to 10.2% by weight
  Complex-forming substance: 0.005 to 15% by weight
  Flow rate of carbonic acid gas: 2000 to 20000 L/H
  Gas concentration: 10 to 100%

(Aging Condition)

Concentration of calcium carbonate: 2.4 to 13.0% by weight

Aging time: 24 to 240 hours

In the aforementioned reaction condition, in order to reduce an average particle diameter (μm) of a particle measured by SALD-2000A laser type particle size distribution meter, a concentration at reaction and aging may be reduced, or an aging time may be prolonged. In order to increase a BET specific surface area (m²/g) measured according to the nitrogen adsorption method, an amount of a complex-forming substance to be added may be increased.

Examples of a silicate compound in the present invention include crystalline silica, hydrous silicic acid, silica by a wet process, silica by a dry process, an alkali metal salt such as sodium or potassium silicate, and an alkaline earth metal salt such as calcium or magnesium silicate, and these may be used alone or in combination of two or more. Wet silica is preferable in that it has an appropriate size and appropriate dispersibility.

Examples of magnesium phosphate in the present invention include monomagnesium phosphate, dimagnesium phosphate, trimagnesium phosphate, and magnesium pyrophosphate, and these may be used alone or in combination of two or more. Trimagnesium phosphate is preferable in that it has an appropriate size and appropriate dispersibility.

Examples of zeolite in the present invention include synthetic zeolite and natural zeolite, and these may be used alone or in combination of two or more. Synthetic zeolite is preferable in that it has an appropriate size and appropriate dispersibility.

Examples of magnesium carbonate in the present invention include basic magnesium carbonate, heavy magnesium carbonate, and light magnesium carbonate. These may be used alone or in combination of two or more. A mixture of calcium carbonate and magnesium carbonate, that is, dolomite may be used. Inter alia, light magnesium carbonate is preferable in that it has an appropriate size and appropriate dispersibility.

An average particle diameter P of the flower thinning agent of the present invention measured by a particle size distribution meter satisfies the following relationship (a), more preferably the relationship (d), further preferably the relationship (g):

$$0.03 \leq P \leq 30 \tag{a}$$

$$0.03 \leq P \leq 10 \tag{d}$$

$$0.03 \leq P \leq 5 \tag{g}$$

When an average particle diameter P exceeds 30 μm, since an additive added to an inorganic composition of poor water solubility is not sufficiently adsorbed, not only durability of effect of the flower thinning agent tends to be insufficient, but also medicine damage is easily caused. On the other hand, a lower limit of an average particle diameter P is not particularly limited, but usually, it is technically difficult to synthesize an inorganic compound of poor water solubility maintaining a state of dispersion of less than 0.03 μm.

In addition, when a size of an inorganic compound of poor water solubility is very small, since a size of a pollen is generally around 20 to 50 cm, an inorganic compound of poor water solubility which is finer than a size of a pollen physically covers a pistil or a stamen, and has effect of preventing pollination. Therefore, a fine inorganic compound of poor water solubility is particularly preferable.

An average particle diameter P of a particle size distribution in the present invention was calculated from an average particle diameter (μm) measured by SALD-2000A laser type particle size distribution meter. A measurement sample was diluted with distilled water so that a concentration of a flower thinning agent became 5% by weight, this was pre-dispersed at 20 kHZ and 300W for 1 minute using an ultrasonic disperser US-300T manufactured by Nippon Seiki Seisakusyo Co., Ltd.), followed by measurement.

A specific surface area Q of the flower thinning agent of the present invention satisfies the following relationship (b), more preferably the relationship (e), further preferably the relationship (h), and a most preferable range is $25 \leq Q \leq 200$.

$$3 \leq Q \leq 800 \tag{b}$$

$$7 \leq Q \leq 300 \tag{e}$$

$$10 \leq Q \leq 200 \tag{h}$$

When a specific surface area Q exceeds 800 m²/g, since a specific surface area becomes too large, there is a tendency that a sustained release rate of an additive added to an inorganic particle of poor water solubility becomes too late, an additive in a mixture preparation is not released at such a sufficient amount that pollination is inhibited at a pollination season of a flower, and flower thinning effect tends to be insufficient. On the other hand, when a specific surface area is less than 3 m²/g, since a specific surface area of the flower thinning agent is too small, an adsorption area of an additive becomes small, not only durability of flower thinning effect tends to be insufficient, but also medicine damage is easily caused.

In the present invention, a specific surface area Q was measured using NOVA2000 manufactured by Yuasa Ionics Inc. A measurement sample was diluted with distilled water so that a concentration of a flower thinning agent became 5% by weight, this was pre-dispersed at 20 kHZ and 300 W for 1 minute using an ultrasound disperser US-300T (manufactured by Nippon Seiki Seisakusyo Co., Ltd.), dried at 350° C. for 3 hours, and passed through a 60 mesh, which was used.

A Q/P value of the flower thinning agent of the present invention satisfies the following relationship (c), more preferably the relationship (f), further preferably the relationship (i):

$$0.5 \leq Q/P \leq 1000 \tag{c}$$

$$0.5 \leq Q/P \leq 300 \tag{f}$$

$$1 \leq Q/P \leq 150 \tag{i}$$

When a Q/P value exceeds 1000, since there is a tendency that it becomes difficult to manifest sustained release effect of an additive added to an inorganic particle of poor water solubility, flower thinning effect becomes insufficient depending on deflection of weather. On the other hand, when a Q/P value is less than 0.5, an adsorption area of an additive becomes too small, not only durability of effect tends to be insufficient, but also medicine damage is easily caused.

In the flower thinning agent of the present invention, a point (ml/g) Dys, in which a mercury penetration increment (Log Differential Intrusion) becomes maximum in a mercury penetration method, satisfies preferably the relationship (j) $0.5 \leq Dys \leq 10$, more preferably $0.5 \leq Dys \leq 8$, further preferably $0.5 \leq Dys \leq 7$. When a point (ml/g) Dys, in which a mercury penetration increment (Log Differential Intrusion) becomes maximum, is less than 0.5, an additive is not sufficiently adsorbed, and flower thinning effect is insufficient in some cases, being not preferable. On the other hand, when Dys exceeds 10, adsorption is too strong, sufficient flower thinning effect is not exerted, being not preferably.

In the flower thinning agent of the present invention, Dxs, which is an average pore diameter of Dys, satisfies preferably the relationship (k) $0.002 \leq Dxs \leq 10$, more preferably the relationship $0.003 \leq Dxs \leq 3$, further preferably the relationship $0.005 \leq Dxs \leq 1$. When Dxs is less than 0.002, there is a tendency that a sustained release rate of an additive added to an inorganic particle of poor water solubility becomes too late, and flower thinning effect tends to be insufficient, being not preferable. On the other hand, when Dxs exceeds 10, durability of sufficient flower thinning effect is not exerted, and medicine damage is easily caused, being not preferable.

In a mercury penetration method, a point (ml/g) Dys, in which a mercury penetration increment (Log Differential Intrusion) becomes maximum, and its average pore diameter Dxs are measured using a mercury penetration apparatus (porosimeter) Model 9520 manufactured by Shimadzu Corporation, and measurement conditions are as follows:

Mercury purity 99.99%
Mercury surface tension 484 dyns/cm
Mercury contact angle 130°
Cell constant 10.79 μl/pF
Sample weight 0.1 to 0.5 g A measurement sample was diluted with distilled water so that a concentration of a flower thinning agent became 5% by weight, this was pre-dispersed at 20 kHZ and 300W for 1 minute using an ultrasound disperser US-300T (manufactured by Nippon Seiki Seisakusyo Co., Ltd.), dried at 350° C. for 3 hours, and passed through a 60 mesh, which was used.

In the flower thinning agent of the present invention, an amount of an average pore diameter Dys/Dxs satisfies preferably the relationship (l) $0.5 \leq Dys/Dxs \leq 300$, more preferably the relationship $1.0 \leq Dys/Dxs \leq 150$, further preferably $3.0 \leq Dys/Dxs \leq 130$. When Dys/Dxs is less than 0.5, carrying effect is small, and persistent flower thinning effect is not obtained in some cases, being not preferable. On the other hand, when Dys/Dxs exceeds 300, adsorption onto an inorganic particle of poor water solubility becomes too strong, and desired flower thinning effect is not obtained in some cases, being not preferable.

In the present invention, R (μm), an average particle diameter measured by an electron microscope, of a flower thinning agent in which an inorganic compound of poor water solubility comprises calcium phosphate, satisfies the following relationship (m), preferably the relationship (o), further preferably the relationship (u):

$$0.01 \leq R \leq 30 \tag{m}$$

$$0.01 \leq R \leq 10 \tag{o}$$

$$0.01 \leq R \leq 5 \tag{u}$$

When an average particle diameter R measured by an electron microscope exceeds 30 μm, an additive added to an inorganic compound of poor water solubility is not sufficiently adsorbed, not only durability of effect tends to be insufficient, but also medicine damage is easily caused. On the other hand, when an average particle diameter R measured by an electron microscope is less than 0.01 μm, there is a tendency that it is difficult to prepare an inorganic compound having suitable dispersibility as an inorganic compound for a flower thinning agent.

When R, an average particle diameter measured by an electron microscope, of the flower thinning agent of the present invention is 0.03 μm or larger, R is obtained by measuring a long diameter and a short diameter of the flower thinning agent present in a range of 3 cm×3 cm at a central part of a photograph with a gauge, in a photograph of magnification of 10000 taken by an electron microscope S-2360N manufactured by Hitachi, Ltd., and obtaining its average. In addition, when a primary particle diameter is less than 0.03 μm, the diameter is obtained by measuring a long diameter and a short diameter of the flower thinning agent present in a range of 3 cm×3 cm at a central part of a photograph with a gauge, in a photograph of magnification of 100000 taken by an electron microscope JEM-200CX manufactured by JEOL. Ltd., and obtaining its average.

A porosity S of a flower thinning agent comprising calcium phosphate satisfies the following relationship (n), more preferably the relationship (t), further preferably the relationship (v):

$$0.5 \leq S \leq 300 \tag{n}$$

$$0.5 \leq S \leq 100 \tag{t}$$

$$0.5 \leq S \leq 10 \tag{v}$$

When a porosity S exceeds 300, since a porosity becomes too high, there is a possibility that a sustained release rate of an additive which has been added to an inorganic compound of poor water solubility becomes too late, an additive in a mixture preparation is not released at a pollination season of a flower at such a sufficient amount that pollination is inhibited at a pollination season of a flower, and it becomes difficult to obtain sufficient sustained release effect. On the other hand, when a porosity S is less than 0.5, since there is a tendency that an aggregation degree of an inorganic compound of poor water solubility is intense and, at the same time, sustained release effect is not expected so much, there is a tendency that a flower thinning agent potentially causes adsorption deficiency of an additive and medicine damage is easily generated.

When calcium phosphate is used in the present invention, a particle having a great porosity can be obtained even if a particle diameter measured by an electron microscope is great, and generally even in the case of a particle diameter easily causing medicine damage, it becomes easy to prevent medicine damage by adjusting porosity, being thus preferable.

Examples of the additive used in the present invention include condensed phosphoric acid and a salt thereof, lecithin, sterol, amino acid, and sucrose fatty acid ester, and these may be used alone or in combination of two or more. In view of a possibility of medicine damage being small, and more efficient effect being easily exerted, at least one kind selected from lecithin and plant sterol is preferable.

Examples of condensed phosphoric acid and a salt thereof used in the present invention include alkali metal salts of pyrophosphoric acid, tripolyphosphoric acid, metaphosphoric acid, and highpolyphosphoric acid. These may be used alone or in combination of them.

Examples of sterol in the present invention include cholesterol as animal sterol, and stigmasterol, siposterol, campesterol, and brassicasterol as plant sterol. From a viewpoint of influence on the environment, the plant sterol is preferable. These may be used alone or in combination of them.

Examples of the amino acid in the present invention include neutral amino acids, acidic amino acids, and basic amino acids. Specifically, examples include glycine, alanine, lysine, glutamic acid, and aspartic acid. These may be used alone or in combination of them.

Examples of lecithin in the present invention include soybean lecithin, yolk lecithin, high purity lecithin, enzyme-degraded lecithin, enzyme-treated lecithin, fractionated lecithin, enzyme-modified lecithin, hydroxylated lecithin, acetylated lecithin, succinylated lecithin, and hydrogenated lecithin. From a viewpoint of flower thinning effect, enzyme-treated lecithin, enzyme-modified lecithin, and enzyme-degraded lecithin are more preferable. These may be used alone or in combination of them.

Sucrose fatty acid ester in the present invention has an HLB of, for example, 1 to 19 and, from a viewpoint that handling is easy in an aqueous system, an HLB of 8 to 19 is preferable. Specific examples include sucrose stearic ester, oleic ester, palmitic ester, myristic ester, palmitic ester, and behenic ester and, from a viewpoint of flower thinning effect, myristic ester and palmitic ester are more preferable. They may be used alone or in combination of them.

A ratio of mixing an inorganic compound of poor water solubility and an additive is preferably such that an additive is in a range of 0.005 to 200 parts by weight per 100 parts by weight of an inorganic compound of poor water solubility. When an additive is at least one kind selected from the following (A) group and is used at a large amount, there is a tendency that browning of a leaf and a petal is easily caused, the additive is used preferably in a range of 0.005 to 10% by weight, more preferably 0.005 to 3 parts by weight, further preferably 0.01 to 0.5 parts by weight.

(A) Group: Sterol

When the additive is at least one kind selected from the following (B) group, the additive is preferably used in a range of 0.5 to 200 parts by weight, more preferably 1 to 100 parts by weight, further preferably 3 to 50 parts by weight.

(B) Group: Condensed Phosphoric Acid and a Salt Thereof, Lecithin, Amino Acid, and Sucrose Fatty Acid Ester When an amount of the additive to be added is less than 0.005 parts by weight per 100 parts by weight of an inorganic compound of poor water solubility, flower thinning effect becomes insufficient, being not preferable. On the other hand, when the amount exceeds 200 parts by weight, there is a tendency that medicine damage such as browning of a leaf and epinasty phenomenon is easily caused, being not preferable.

If necessary, one kind or two or more kinds of acetic acid, gluconic acid, lactic acid, tartaric acid, succinic acid, fumaric acid, malic acid, glutamic acid, adipic acid, and citric acid, and a salt thereof may be further contained in the flower thinning agent of the present invention.

The flower thinning agent of the present invention may be used by diluting with a buffer. In this respect, thereupon, when a pH is between 4 and 10, there is no particular problem, but, when influence on a human body and a fruit tree is taken into consideration, the flower thinning agent is preferably used in a range of a pH 4.5 to 8.5, more preferably in a range of a pH 5.5 to 8.0. As the buffer, a phosphate buffer, and a carbonate buffer are preferably used.

The flower thinning agent of the present invention can be used in an arbitrary state such as a water-dispersible powder, a fine or crude powder, an emulsion or a flowable agent.

For the purpose of improving solubility, if necessary, in the flower thinning agent of the present invention, an emulsifying agent, a polysaccharide, an oligosaccharide, a sugar alcohol, a surfactant, and a processed starch may be used alone or in combination of two or more.

Examples of the emulsifying agent include polyglycerin fatty acid ester, monoglycerin fatty acid ester, and sorbitan fatty acid ester.

Examples of the polysaccharide include a polymer containing more than 10 monosaccharide residues such as a viscosity increasing polysaccharide and a soybean polysaccharide. Examples of the viscosity increasing polysaccharide include welan gum, carrageenan gum, sodium alginate, guar gum, gelan gum, karaya gum, CMC, methylcellulose, tamarind gum, guddy gum, tragacanth gum, xanthan gum, pullulan gum, cassia gum, rocustbean gum, arabinogalactan, sclerotium gum, and chitosan. The soybean polysaccharide is a water-soluble polysaccharide extracted from a soybean and, inter alia, a polysaccharide composed of galactose, galacturonic acid, rhamnose, xylose, fucose, and glucose, having an average molecular weight of a few hundreds of thousands is preferable.

Examples of the oligosaccharide include a polymer containing 2 to 10 monosaccharide residues such as reducing or non-reducing saccharides, and specific examples include trehalose, trehalrose, maltose, cellobiose, lactose, xylobiose, isomaltose, melibiose, palatinose, gentibiose, maltooligosaccharide, isooligosaccharide, glucooligosaccharide, galactooligosaccharide, soybeanoligosaccharide, xylooligosaccharide, lactooligosaccharide, fructooligosaccharide, and coupling sugar.

The sugar alcohol is not particularly limited, it is a chain polyhydric alcohol obtained by reducing a carbonyl group possessed by saccharides, and specific examples include maltitol, palatinit, lactitol, erythitol, xylitol, mannitol, and sorbitol.

Examples of the surfactant include the known cationic, anionic, amphoteric or nonionic organic surfactants and inorganic surfactants.

The processed starch is starch that is processed chemically or physically, and examples include acid-treated starch, alkali-treated starch, oxidized starch, cyclodextrin, dextrin, enzyme-treated starch, phosphoric acid esterified starch, acetate starch, octenylsuccinic acid starch, etherized starch, and crosslinked starch.

As described above, since the previous flower thinning agent is a water-soluble flower thinning agent, for example, when a preferable spread season is rainy, the flower thinning agent is easily flown away, and flower thinning effect is hardly expected. However, since the flower thinning agent of the present invention is composed of a particular inorganic compound of poor water solubility and an additive, and the additive is in the immersed or adsorbed state, it has an advantage that it is hardly flown away as compared with the previous flower thinning agent. Further, by using a substance having binding effect such as polyvinyl alcohol, polybutene, and carboxymethylcellulose together with the flower thinning agent of the present invention, flowing away preventing effect at rainy weather can be further improved.

A preferable method of spreading the flower thinning agent of the present invention to a fruit tree will be explained. In flowering of a defoliation fruit such as an apple, a central flower at an apical bud is first in full bloom, thereafter, a lateral flower at an apical bud is in full bloom slightly later and, further after a few days to one week, an axillary flower is in full bloom. The flower thinning agent of the present invention may be spread when a central flower at an apical bud is full bloom and, if necessary, a spread term may be slightly shifted before and after.

Since the previous flower thinning agent is water-soluble, when the flower thinning agent is used, the flower thinning agent is easily flown away. Therefore, there is a problem that not only durability of effect is short, but also effect is scattered due to fine deflection of spread timing. However, when the flower thinning agent of the present invention is used, since it is composed of a particular inorganic compound of poor water solubility and an additive, and the additive is in the immersed or adsorbed state, durability of a medicine is high, therefore, the flower thinning agent of the present invention is excellent over the previous flower thinning agent in that even when flowering timing is slightly deflected due to a change in weather, it can respond thereto.

The flower thinning agent of the present invention not only has no adverse effect on the environment, but also has little possibility of medicine damage, and hardly undergoes influence of a district or weather, and can be used in apple, pear, peach, grape, persimmon, and citrus fruit.

Alternatively, the flower thinning agent of the present invention may be used by mixing with other agricultural drug such as an insecticide, or a. fertilizer.

The present invention will be explained in more detail below by way of Examples, and Comparative Examples, but the present invention is not limited to these Examples. Hereinafter, % and part are based on a weight unless otherwise indicated.

Calcium carbonate, calcium phosphate, magnesium phosphate, and zeolite used in the present Examples, and Comparative Examples were prepared by the following processes.

Calcium Carbonate I

Citric acid was added to 11% lime milk at 0.1% relative to a lime milk solid matter, a carbonic acid gas having a concentration of 25% was introduced therein to perform a carbonization reaction, a carbonization reaction was stopped at a pH of a system of 9.5, this was stirred at 50° C. for 15 hours, and a carbonic acid gas was introduced again to adjust a pH of a system to 7 or lower, to obtain a white slurry. The white slurry was dehydrated with a filter press to obtain calcium carbonate I. It was confirmed by X-ray diffraction that the resulting white cake is calcite type calcium carbonate.

Calcium Carbonate II

A 25% carbonic acid gas was introduced into 11% lime milk to perform a carbonization reaction, a carbonization reaction is stopped at a pH of a system of 8, this was stirred at 50° C. for 15 hours, and a carbonic acid gas was introduced again to adjust a pH of a system to 8 or lower, to obtain a calcium carbonate slurry. Then, 1.5 L of 11% calcium hydroxide was added to 1 L of the calcium carbonate slurry, and a carbonic acid gas was introduced again to adjust a pH of a system to 7, to obtain a white slurry. The white slurry was dehydrated using a filter press, and dried at 180° C. to obtain calcium carbonate II. It was confirmed by X-ray diffraction that the resulting white substance is calcite type calcium carbonate.

Calcium Carbonate III

A carbonic acid gas having a concentration of 25% was introduced into 11% lime milk to perform a carbonization reaction, a carbonization reaction was stopped at a pH of a system of 9.5, this was stirred at 50° C. for 5 hours, and a carbonic acid gas was introduced again to adjust a pH of a system to 7 or lower, to obtain a white slurry. The white slurry was dehydrated with a filter press to obtain calcium carbonate III. It was confirmed by X-ray diffraction that the resulting white cake is calcite type calcium carbonate.

Calcium Carbonate IV

Citric acid was added to 10% lime milk at 2% relative to a lime milk solid matter, a carbonic acid gas having a concentration of 20% was introduced to perform a carbonization reaction, a carbonization reaction was stopped at a pH of a system of 9.5, this was stirred at 50° C. for 5 hours, and a carbonic acid gas was introduced again to adjust a pH of a system to 7 or lower, to obtain a white slurry. The white slurry was dehydrated with a filter press to obtain calcium carbonate IV. It was confirmed by X-ray diffraction that the resulting white cake is calcite type calcium carbonate.

Calcium Phosphate I

10% phosphoric acid was added dropwise to a 20% aqueous slurry of calcium carbonate (Super #2000, manufactured by Maruo Calcium Company Limited) at a Ca/P mole ratio=3.33 under stirring aid, thereafter, this was stirred at 50° C. for 3 hours to obtain a white slurry. The white slurry was dehydrated using a filter press to obtain calcium phosphate I. It was confirmed by X-ray diffraction that the resulting white cake is a mixture of hydroxyapatite and calcite type calcium carbonate.

Calcium Phosphate II

10% phosphoric acid was added dropwise to a 20% aqueous slurry of calcium carbonate (heavy calcium carbonate, manufactured by Maruo Calcium Company Limited) at a Ca/P mole ratio=4.00 under stirring and, thereafter, this was stirred at 50° C. for 3 hours to obtain a white slurry. The white slurry was dehydrated using a filter press, and dried at 180° C. to obtain calcium phosphate II. It was confirmed by X-ray diffraction that the resulting white powder is a mixture of hydroxyapatite and calcite type calcium carbonate.

Calcium Phosphate III 0.05 mol of 50% citric acid was added dropwise to 1 mol of a 11% calcium hydroxide slurry regulated at 15° C. over 300 seconds under stirring, thereafter, a mixture of 0.66 mol of 30% phosphoric acid and 0.15 mol of 40% KOH was added dropwise over 600 seconds and, thereafter, this was stirred at 80° C. for 3 hours to obtain calcium phosphate III. It was confirmed by X-ray diffraction that the resulting white substance is amorphous calcium phosphate.

Calcium Phosphate IV 0.05 mol of 50% citric acid was added dropwise to 1 mol of a 11% calcium hydroxide slurry regulated at 15° C. over 300 seconds under stirring, thereafter, a mixture of 0.66 mol of 30% phosphoric acid and 0.05 mol of 40% KOH was added dropwise over 600 seconds and, thereafter, this was stirred at 80° C. for 3 hours to obtain a white slurry. The white slurry was dried with a spray drier to obtain calcium phosphate IV. It was confirmed by X-ray diffraction that the resulting white powder is amorphous calcium phosphate.

Calcium Phosphate V 0.05 mol of 50% citric acid was added dropwise to 1 mol of a 11% calcium hydroxide slurry regulated at 15° C. over 300 seconds under stirring, thereafter, a mixture of 0.66 mol of 30% phosphoric acid and 0.05 mol of 40% KOH was added dropwise over 600 seconds and, thereafter, this was stirred at 80° C. for 3 hours to obtain a white slurry. The slurry was concentrated to a solid matter of 50% using an ultracentrifuge, and water was added again to obtain a slurry having-the same concentration as that before concentrated. The aforementioned concentration and re-slurrying were repeated three times to obtain calcium phosphate V. It was confirmed by X-ray diffraction that the resulting white cake is amorphous calcium phosphate.

Calcium Phosphate VI

10% phosphoric acid was added dropwise to a 20% aqueous slurry of calcium carbonate (Calsee F, manufactured by Sankyo Seifun) at a Ca/P mole ratio=3.00 under stirring, and thereafter, this was stirred at 50° C. for 3 hours to obtain a white slurry. The white slurry was dehydrated using a filter press to obtain calcium phosphate VI. It was confirmed by X-ray diffraction that the resulting white powder cake is a mixture of hydroxyapatite and calcite type calcium carbonate.

Calcium Phosphate VII

10% phosphoric acid was added dropwise to a 20% aqueous slurry of calcium carbonate (No. A Ground Calcium Carbonate, manufactured by Maruo Calcium Company Limited) at a Ca/P mole ratio=5.00 under stirring and, thereafter, this was stirred at 50° C. for 3 hours to obtain a white slurry. The white slurry was dehydrated using a filter press to obtain calcium phosphate VII. It was confirmed by X-ray diffraction that the resulting white powder is a mixture of hydroxyapatite and calcite type calcium carbonate.

Magnesium Phosphate 0.66 mol of 30% phosphoric acid was added dropwise to 1 mol of magnesium hydroxide (manufactured by Maruo Calcium Company Limited) at 15° C. over 600 seconds under stirring and, thereafter, this was stirred at 80° C. for 3 hours to obtain a white slurry. The white slurry was washed and dehydrated with a rotary filter to obtain magnesium phosphate. It was confirmed by X-ray diffraction that the resulting white cake is trimagnesium phosphate.

Zeolite

Natural zeolite was ground with an H mill, and classified to obtain zeolite I.

EXAMPLE 1

Using the aforementioned calcium carbonate I, 40 parts of glycine and water were added to calcium carbonate I (100 parts in terms of a calcium carbonate solid matter), and this was stirred and mixed to obtain a flower thinning agent having a 30% of calcium carbonate solid matter concentration. P(μm): an average particle diameter of a particle measured by a SALD-2000A laser type particle size distribution meter, Q($m^2$/g): a BET specific surface area measured according to the nitrogen adsorption method, Q/P, Dys, Dxs, and Dys/Dxs of the resulting flower thinning agent are shown in Table 1.

EXAMPLES 2 TO 4, 6 TO 11, 13, 14, 16, 18 AND 19, AND COMPARATIVE EXAMPLES 1, 2, AND 4 TO 7

According to the same manner as that of Example 1 except that an inorganic compound of poor water solubility was changed as in Table 1, and a kind of an additive and a part by weight of addition were changed as in Table 1, the flower thinning agents were obtained. P(μm): an average particle diameter of a particle measured by a SALD-2000A laser type particle size distribution meter, Q($m^2$/g): a BET specific surface area measured according to the nitrogen adsorption method, Q/P, Dys, Dxs, and Dys/Dxs of the resulting flower thinning agent are shown in Table 1 and Table 2. Regarding the flower thinning agents in which the inorganic compound of poor water solubility is calcium phosphate, an average particle diameter (μm) R measured by an electron micrograph, and a porosity S are shown in Table 3.

EXAMPLE 5

Using the aforementioned calcium carbonate III, 0.05 part of sterol A was added to calcium carbonate III (100 parts in terms of a calcium carbonate solid matter), and this was stirred and mixed to obtain a flower thinning agent having a calcium carbonate solid matter concentration of 10%. P(μm): an average particle diameter of a particle measured by a SALD-2000A laser type particle size distribution meter, Q($m^2$/g): a BET specific surface area measured according to the nitrogen adsorption method, Q/P, Dys, Dxs, and Dys/Dxs of the resulting flower thinning agent are shown in Table 1.

Sterol A was dissolved in a 10% pentaglycerin fatty acid ester solution at 65° C. at a solid matter weight ratio of 1:30.

EXAMPLES 12, 15 AND 17, AND COMPARATIVE EXAMPLES 3 AND 8

According to the same manner as that of Example 5 except that an inorganic compound of poor water solubility was changed as in Table 1 and Table 2, and a kind of an additive and a part by weight of addition were changed as in Table 1 and Table 2, flower thinning agents were obtained. P(μm): an average particle diameter of a particle measured by a SALD-2000A laser type particle size distribution meter, Q($m^2$/g): a BET specific surface area measured according to the nitrogen adsorption method, Q/P, Dys, Dxs, and Dys/Dxs of the resulting flower thinning agent are shown in Table 1 and Table 2. Regarding the flower thinning agents in which the inorganic compound of poor water solubility is calcium phosphate, an average particle diameter (μm) R of a particle measured by an electron micrograph, and a porosity S are shown in Table 3.

EXAMPLES 20 AND 21, AND COMPARATIVE EXAMPLES 9 AND 10

Each of the flower thinning agents prepared in Examples 7 and 12 and Comparative Examples 1 and 5 was dried with a spray drier to obtain a flower thinning agent powder. In Example 20 and Comparative Example 9, before drying, 10 parts of arabic gum was added to 100 parts of an inorganic compound, and this was dried.

P(μm): an average particle diameter of a particle measured by a SALD-2000A laser type particle size distribution meter, Q($m^2$/g): a BET specific surface area measured according to the nitrogen adsorption method, Q/P, Dys, Dxs, Dys/Dxs, an average particle diameter (μm) R of a particle measured by an electron micrograph, and a porosity S of the resulting flower thinning agents are shown in Table 1 to Table 3.

TABLE 1

|  | Inorganic compound of poor water solubility | Additive | | Characteristics of flower thinning agent | | | | | |
|---|---|---|---|---|---|---|---|---|---|
|  |  | Kind | Parts | P μm | Q $m^2$/g | Q/P | Dys | Dxs | Dys/Dxs |
| Ex. 1 | calcium carbonate I | glycine | 40 | 1.43 | 26.2 | 18.3 | 2.16 | 0.030 | 72.00 |
| Ex. 2 | calcium carbonate II | S E | 0.3 | 5.12 | 4.2 | 0.8 | 2.23 | 1.054 | 2.12 |
| Ex. 3 | heavy calcium carbonate I | sodium hexametaphosphate | 180 | 1.45 | 5.7 | 3.9 | 1.50 | 0.350 | 4.28 |
| Ex. 4 | calcium phosphate III | high purity lecithin | 45 | 1.58 | 80.3 | 50.8 | 1.62 | 0.015 | 108.00 |
| Ex. 5 | calcium carbonate III | sterol A | 0.05 | 1.20 | 18.2 | 15.2 | 1.74 | 0.045 | 38.67 |
| Ex. 6 | calcium phosphate IV | high purity lecithin | 1.5 | 1.62 | 189.3 | 48.9 | 1.81 | 0.018 | 100.56 |
| Ex. 7 | magnesium phosphate | enzyme-degraded lecithin sterol A | 20 0.02 | 2.36 | 95.1 | 40.3 | 0.98 | 0.009 | 102.22 |
| Ex. 8 | tricalcium phosphate | enzyme-treated lecithine | 30 | 2.18 | 51.3 | 23.5 | 0.89 | 0.052 | 17.12 |
| Ex. 9 | silica I | sterol B | 0.05 | 2.75 | 721.5 | 262.4 | 1.92 | 0.350 | 5.49 |
| Ex. 10 | silica II | enzyme-degraded lecithin | 20 | 0.33 | 126.5 | 383.3 | 7.68 | 0.066 | 116.36 |

TABLE 1-continued

| | Inorganic compound of poor water solubility | Additive Kind | Parts | Characteristics of flower thinning agent | | | | | |
|---|---|---|---|---|---|---|---|---|---|
| | | | | P μm | Q m²/g | Q/P | Dys | Dxs | Dys/Dxs |
| Ex. 11 | calcium phosphate V | hydroxylated lecithin | 90 | 1.58 | 92.3 | 58.4 | 1.48 | 0.015 | 98.67 |
| Ex. 12 | calcium phosphate I | sterol A | 0.04 | 6.10 | 90.3 | 14.8 | 5.02 | 1.636 | 3.07 |
| Ex. 13 | calcium carbonate II | S E | 210 | 5.25 | 4.0 | 0.8 | 2.35 | 1.054 | 2.23 |
| Ex. 14 | calcium phosphate VI | high purity lecithin S E | 20 25 | 1.39 | 129.3 | 93.0 | 3.21 | 1.636 | 1.96 |
| Ex. 15 | magnesium carbonate | sterol A | 0.008 | 2.18 | 23.4 | 10.7 | 2.09 | 3.19 | 0.66 |
| Ex. 16 | zeolite I | high purity lecithin | 20 | 28.62 | 38.3 | 1.3 | 0.98 | 0.921 | 1.06 |
| Ex. 17 | calcium phosphate II | sterol A | 2.8 | 13.18 | 44.3 | 3.4 | 3.21 | 2.102 | 1.53 |
| Ex. 18 | silica III | high purity lecithin | 10 | 2.52 | 277.9 | 110.3 | 2.1 | 0.284 | 7.39 |
| Ex. 19 | calcium carbonate IV | enzyme-degraded lecithin | 15 | 1.47 | 43.5 | 29.6 | 1.71 | 0.020 | 85.5 |
| Ex. 20 | magnesium phosphate | enzyme-degraded lecithin sterol A | 20 0.02 | 2.45 | 92.6 | 37.6 | 1.01 | 0.010 | 101.00 |
| Ex. 21 | calcium phosphate I | sterol A | 0.04 | 6.02 | 90.0 | 15.0 | 5.21 | 1.626 | 3.20 |

P: Average particle diameter
Q: BET specific surface area

P: Average particle diameter (μm) of particle measured by SALD-2000A laser type particle size distribution meter Q: BET specific surface area (m²/g) measured according to the nitrogen adsorption method Dys: Point (ml/g) in which a mercury penetration increment (Log Differential Intrusion) becomes maximum in a mercury penetration method Dxs: Average pore diameter of (μm) Dys Heavy calcium carbonate I: R Jutan (Ground Calcium Carbonate, manufactured by Maruo Calcium Company Limited)

Tricalcium phosphate: Tricalcium phosphate (manufactured by Taihei Chemical Industrial Co., Ltd)

Silica I: CX-200 (manufactured by Nihon Silica Corporation)

Silica II: Aerosil 130 (manufactured by Nippon Aerosil Co., Ltd)

Silica III: AZ400 (manufactured by Nihon Silica Corporation)

Magnesium carbonate: Heavy magnesium carbonate (manufactured by Tomita Pharmaceutical Co., Ltd)

Enzyme-degraded lecithin: SLP-Pastelyso (manufactured by T&K Lecithin)

High purity lecithin: SLP-White (manufactured by T&K Lecithin)

Sterol A: GENEROL100 (manufactured by Cognis Japan)

Sterol B: Animal sterol

SE: Sucrose stearic acid ester (manufactured by Mitsubishi-Kagaku Foods Corporation)

Sodium hexametaphosphate: Sodium hexametaphosphate (manufactured by Taihei Chemical Industrial Co., Ltd)

Hydroxylated lecithin: Hydroxylated lecithin (manufactured by T&K lecithin)

TABLE 2

| | Inorganic compound of poor water solubility | Additive Kind | Parts | Characteristics of flower thinning agent | | | | | |
|---|---|---|---|---|---|---|---|---|---|
| | | | | P μm | Q m²/g | Q/P | Dys | Dxs | Dys/Dxs |
| Comp. Ex. 1 | heavy calcium carbonate II | S E | 10 | 21.3 | 0.5 | 0.02 | 0.70 | 3.882 | 0.18 |
| Comp. Ex. 2 | heavy calcium carbonate III | high purity lecithin | 45 | 4.36 | 1.3 | 0.3 | 1.27 | 0.919 | 1.38 |
| Comp. Ex. 3 | zeolite II | sterol A | 0.1 | 6.10 | 810.5 | 132.9 | 2.15 | 0.019 | 113.16 |
| Comp. Ex. 4 | calcium phosphate VII | high purity lecithin | 10 | 48.21 | 48.0 | 1.00 | 3.99 | 2.06 | 0.77 |
| Comp. Ex. 5 | calcium hydrogen phosphate I | enzyme-degraded lecithin | 40 | 70.32 | 0.3 | 0.004 | 2.88 | 15.774 | 0.18 |
| Comp. Ex. 6 | silica I | — | — | 2.83 | 722.9 | 255.4 | 1.87 | 0.350 | 5.34 |
| Comp. Ex. 7 | calcium phosphate I | — | — | 6.25 | 88.0 | 14.1 | 4.99 | 1.636 | 3.05 |
| Comp. Ex. 8 | calcium hydrogen phosphate II | sterol A | 0.05 | 42.81 | 2.1 | 0.05 | 3.11 | 13.949 | 0.22 |
| Comp. Ex. 9 | heavy calcium carbonate II | S E | 10 | 23.0 | 0.5 | 0.02 | 0.67 | 3.882 | 0.17 |
| Comp. Ex. 10 | calcium hydrogen phosphate I | enzyme-degraded lecithin | 40 | 72.11 | 0.3 | 0.004 | 2.13 | 15.102 | 0.14 |

P: Average particle diameter
Q: BET specific surface area

P: Average particle diameter (μm) of particle measured by SALD-2000A laser type particle size distribution meter Q: BET specific surface area ($m^2/g$) measured according to the nitrogen adsorption method Dys: Point (ml/g) in which mercury penetration increment (Log Differential Intrusion) becomes maximum in mercury penetration method Dxs: Average pore diameter (μm) of Dys Heavy calcium carbonate II: R Jutan (Ground Calcium Carbonate, manufactured by Maruo Calcium Company Limited)

Heavy calcium carbonate III: Super SS (manufactured by Maruo Calcium Company Limited)

Zeolite II: HSZ320NAA (manufactured by Tosoh Corporation)

Calcium hydrogen phosphate I: Calcium monohydrogen phosphate guaranteed reagent (manufactured by Wako Pure Chemical Industries, Ltd.)

Silica I: CX-200 (manufactured by Nihon Silica Corporation)

Calcium hydrogen phosphate II: Calcium monohydrogen phosphate (manufactured by Taihei Chemical Industrial Co., Ltd)

SE: Sucrose stearic acid ester (manufactured by Mitsubishi-Kagaku Foods Corporation)

High purity lecithin: SLP-White (manufactured by T&K lecithin)

Sterol A: GENEROL100 (manufactured by Cognis Japan)

Enzyme-degraded lecithin: SLP-Pastelyso (manufactured by T&K Lecithin)

Q: BET specific surface area ($m^2/g$) measured according to the nitrogen adsorption method R: Average particle diameter (μm) of particle measured by electron micrograph S: Porosity (specific surface area Q1($m^2/g$) calculated by Q/R)

APPLICATION EXAMPLE 1

Using an apple (Fuji) tree, flower thinning effect was confirmed. That is, using the aforementioned apple tree, the flower thinning agent of Example 1 was spread at a concentration shown in Table 4 two times, one day and three days after full blooming of a central flower. An effective ingredient concentration was based on a solid matter weight of an inorganic compound of poor water solubility. Treatment was every branch treatment, and the agent was spread with a back loading sprayer.

Assessment was expressed by a remaining fruit rate regarding a central flower and a lateral flower. Regarding medicine damage, results of observation of a leaf state such as defoliation, discolored leaf and deformed leaf are expressed by the following five stages. Results are shown in Table 4.

◉: Normal
○: Extremely small damage
□: Small damage
Δ: Intermediate damage
×: Great damage

APPLICATION EXAMPLES 2 TO 21, AND COMPARATIVE APPLICATION EXAMPLES 1 TO 10

According to the same manner as that of Application Example 1 except that each of the flower thinning agents of

TABLE 3

| | Inorganic compound of poor water solubility | Additive Kind | Parts | Characteristics of flower thinning agent R μm | Q1 $m^2/g$ | Q $m^2/g$ | Porosity S |
|---|---|---|---|---|---|---|---|
| Ex. 4 | calcium phosphate III | high purity lecithin | 45 | 0.03 | 63.7 | 80.3 | 1.3 |
| Ex. 6 | calcium phosphate IV | high purity lecithin | 1.5 | 0.04 | 47.8 | 189.3 | 4.0 |
| Ex. 8 | tricalcium phosphate | enzyme-treated lecithine | 30 | 0.06 | 31.8 | 51.3 | 1.4 |
| Ex. 11 | calcium phosphate V | hydroxylated lecithin | 90 | 0.03 | 63.7 | 92.3 | 1.5 |
| Ex. 12 | calcium phosphate I | sterol A | 0.04 | 6.00 | 0.32 | 90.3 | 282.2 |
| Ex. 14 | calcium phosphate VI | high purity lecithin S E | 20 25 | 1.28 | 1.5 | 129.3 | 86.3 |
| Ex. 17 | calcium phosphate II | sterol A | 2.8 | 12.02 | 0.16 | 44.3 | 276.9 |
| Ex. 21 | calcium phosphate I | sterol A | 0.04 | 6.10 | 0.32 | 90.0 | 281.2 |
| Comp. Ex. 4 | calcium phosphate VII | high purity lecithin | 10 | 42.25 | 0.05 | 48.0 | 960.0 |
| Comp. Ex. 5 | calcium hydrogen phosphate I | enzyme-degraded lecithin | 40 | 72.3 | 0.03 | 0.3 | 10.0 |
| Comp. Ex. 7 | calcium phosphate I | — | — | 6.11 | 0.32 | 88.0 | 275.0 |
| Comp. Ex. 8 | calcium hydrogen phosphate II | sterol A | 0.05 | 45.25 | 0.04 | 2.1 | 52.5 |
| Comp. Ex. 10 | calcium hydrogen phosphate I | enzyme-degraded lecithin | 40 | 75.73 | 0.03 | 0.3 | 10.0 |

R: Average particle diameter
Q1: Specific surface area Q1 calculated from R
Q: BET specific surface area Examples 2 to 21, and Comparative Examples 1 to 10 was used in place of the flower thinning agent of Example 1, an experiment was performed. Results are shown in Table 4 and Table 5.

COMPARATIVE APPLICATION EXAMPLE 11

According to the same manner as that of Application Example 1 except that a flower thinning agent containing a lime sulfur agent as an effective ingredient was used in place of the flower thinning agent of Example 1, an experiment was performed. An effective ingredient concentration was based on a solid matter weight of a lime and sulfur mixture. Results are shown in Table 5.

COMPARATIVE APPLICATION EXAMPLE 12

According to the same manner as that of Application Example 1 except that a flower thinning agent containing itaconic acid as an effective ingredient was used in place of the flower thinning agent of Example 1, an experiment was performed. An effective ingredient concentration was based on a solid matter weight of itaconic acid. Results are shown in Table 5.

COMPARATIVE APPLICATION EXAMPLE 13

According to the same manner as that of Application Example 1 except that a flower thinning agent containing high purity lecithin as an effective ingredient was used in place of the flower thinning agent of Example 1, an experiment was performed. An effective ingredient concentration was based on a solid matter weight of high purity lecithin. Results are shown in Table 5.

COMPARATIVE APPLICATION EXAMPLE 14

According to the same manner as that of Application Example 1 except that water (control) was used in place of the flower thinning agent of Example 1, an experiment was performed. Results are shown in Table 5.

TABLE 4

| | Flower thinning agent used | Effective ingredient conc. (%) | Fruition rate (%) Lateral flower | Fruition rate (%) Central flower | medicine damage |
|---|---|---|---|---|---|
| Appln. Ex. 1 | Agent of Ex. 1 | 0.33 | 49.3 | 91.3 | ⊚ |
| | | 1.00 | 47.1 | 89.9 | ⊚ |
| Appln. Ex. 2 | Agent of Ex. 2 | 0.33 | 64.9 | 92.3 | ⊚ |
| | | 1.00 | 60.2 | 88.5 | ⊚ |
| Appln. Ex. 3 | Agent of Ex. 3 | 0.33 | 52.3 | 90.3 | ○ |
| | | 1.00 | 49.8 | 88.1 | □ |
| Appln. Ex. 4 | Agent of Ex. 4 | 0.33 | 39.2 | 90.1 | ⊚ |
| | | 1.00 | 38.6 | 89.9 | ⊚ |
| Appln. Ex. 5 | Agent of Ex. 5 | 0.33 | 54.0 | 88.5 | ⊚ |
| | | 1.00 | 51.1 | 87.2 | ⊚ |
| Appln. Ex. 6 | Agent of Ex. 6 | 0.33 | 48.5 | 90.2 | ⊚ |
| | | 1.00 | 45.9 | 89.9 | ⊚ |
| Appln. Ex. 7 | Agent of Ex. 7 | 0.33 | 37.6 | 90.6 | ⊚ |
| | | 1.00 | 35.8 | 86.3 | ⊚ |
| Appln. Ex. 8 | Agent of Ex. 8 | 0.33 | 42.3 | 93.2 | ⊚ |
| | | 1.00 | 39.9 | 89.1 | ⊚ |
| Appln. Ex. 9 | Agent of Ex. 9 | 0.33 | 64.3 | 89.3 | ⊚ |
| | | 1.00 | 59.2 | 88.2 | ⊚ |
| Appln. Ex. 10 | Agent of Ex. 10 | 0.33 | 51.3 | 91.2 | ⊚ |
| | | 1.00 | 49.5 | 89.3 | ⊚ |
| Appln. Ex. 11 | Agent of Ex. 11 | 0.33 | 41.3 | 87.3 | ⊚ |
| | | 1.00 | 39.8 | 86.9 | ○ |
| Appln. Ex. 12 | Agent of Ex. 12 | 0.33 | 54.9 | 86.3 | ⊚ |
| | | 1.00 | 51.2 | 86.5 | ⊚ |
| Appln. Ex. 13 | Agent of Ex. 13 | 0.33 | 48.2 | 90.3 | □ |
| | | 1.00 | 46.8 | 88.4 | □ |
| Appln. Ex. 14 | Agent of Ex. 14 | 0.33 | 46.2 | 90.1 | ⊚ |
| | | 1.00 | 44.6 | 88.9 | ⊚ |
| Appln. Ex. 15 | Agent of Ex. 15 | 0.33 | 47.5 | 91.4 | ⊚ |
| | | 1.00 | 43.3 | 89.2 | ⊚ |
| Appln. Ex. 16 | Agent of Ex. 16 | 0.33 | 45.2 | 90.2 | ○ |
| | | 1.00 | 42.5 | 89.9 | ○ |
| Appln. Ex. 17 | Agent of Ex. 17 | 0.33 | 54.6 | 91.6 | ⊚ |
| | | 1.00 | 48.0 | 88.8 | ○ |
| Appln. Ex. 18 | Agent of Ex. 18 | 0.33 | 52.2 | 91.1 | ⊚ |
| | | 1.00 | 49.6 | 88.9 | ⊚ |
| Appln. Ex. 19 | Agent of Ex. 19 | 0.33 | 42.1 | 91.6 | ⊚ |
| | | 1.00 | 40.2 | 88.9 | ⊚ |
| Appln. Ex. 20 | Agent of Ex. 20 | 0.33 | 40.9 | 88.3 | ⊚ |
| | | 1.00 | 36.2 | 88.2 | ⊚ |
| Appln. Ex. 21 | Agent of Ex. 21 | 0.33 | 54.1 | 87.3 | ⊚ |
| | | 1.00 | 50.2 | 86.5 | ⊚ |

TABLE 5

| | Flower thinning agent used | Effective ingredient conc. (%) | Fruition rate (%) Lateral flower | Fruition rate (%) Central flower | medicine damage |
|---|---|---|---|---|---|
| Comp. Appln. Ex. 1 | Agent of Comp. Ex. 1 | 0.33 | 65.3 | 90.2 | □ |
| | | 1.00 | 63.8 | 88.2 | Δ |
| Comp. Appln. Ex. 2 | Agent of Comp. Ex. 2 | 0.33 | 62.9 | 91.1 | Δ |
| | | 1.00 | 60.2 | 87.5 | Δ |
| Comp. Appln. Ex. 3 | Agent of Comp. Ex. 3 | 0.33 | 81.8 | 91.3 | ⊚ |
| | | 1.00 | 78.1 | 92.1 | ⊚ |
| Comp. Appln. Ex. 4 | Agent of Comp. Ex. 4 | 0.33 | 64.6 | 91.5 | Δ |
| | | 1.00 | 63.6 | 90.9 | Δ |
| Comp. Appln. Ex. 5 | Agent of Comp. Ex. 5 | 0.33 | 65.2 | 89.5 | Δ |
| | | 1.00 | 62.9 | 87.3 | Δ |
| Comp. Appln. Ex. 6 | Agent of Comp. Ex. 6 | 0.33 | 78.2 | 92.2 | ⊚ |
| | | 1.00 | 75.9 | 90.2 | ⊚ |
| Comp. Appln. Ex. 7 | Agent of Comp. Ex. 7 | 0.33 | 81.1 | 92.9 | ⊚ |
| | | 1.00 | 79.2 | 91.3 | ⊚ |
| Comp. Appln. Ex. 8 | Agent of Comp. Ex. 8 | 0.33 | 61.2 | 89.5 | Δ |
| | | 1.00 | 59.9 | 87.3 | Δ |

TABLE 5-continued

| | Flower thinning agent used | Effective ingredient conc. (%) | Fruition rate (%) Lateral flower | Central flower | medicine damage |
|---|---|---|---|---|---|
| Comp. Appln. Ex. 9 | Agent of Comp. Ex. 9 | 0.33 | 65.3 | 90.2 | □ |
| | | 1.00 | 63.8 | 88.2 | Δ |
| Comp. Appln. Ex. 10 | Agent of Comp. Ex. 10 | 0.33 | 66.2 | 90.5 | Δ |
| | | 1.00 | 62.0 | 89.1 | Δ |
| Comp. Appln. Ex. 11 | Agent containing a lime sulfur | 0.33 | 55.2 | 88.3 | Δ |
| | | 1.00 | 49.1 | 84.2 | Δ |
| Comp. Appln. Ex. 12 | Agent containing itaconic acid | 0.33 | 57.9 | 88.2 | Δ |
| | | 1.00 | 50.3 | 85.4 | X |
| Comp. Appln. Ex. 13 | Agent containing high purity lecithin | 0.15 | 65.9 | 88.2 | Δ |
| | | 0.45 | 60.3 | 85.4 | Δ |
| Comp. Appln. Ex. 14 | Water (control) | — | 88.2 | 93.1 | ⊚ |

APPLICATION EXAMPLE 22

Using a pear (Kosui) tree, flower thinning effect was confirmed. That is, using the aforementioned pear tree, the flower thinning agent of Example 1 was spread at a concentration indicated in Table 6 two times, at a flowering rate of 30% and 80%. An effective ingredient concentration was based on a solid matter weight of an inorganic compound of poor water solubility. Treatment was every branch treatment, and the agent was spread with a back loading sprayer.

Assessment was expressed as a remaining fruit rate relative to the number of flowering. Regarding medicine damage, results of observation of a leaf state such as defoliation, discolored leaf and deformed leaf were expressed by the following five stages. Results are shown in Table 6.

⊚: Normal
○: Extremely small damage
□: Small damage
Δ: Intermediate damage
×: Large damage

APPLICATION EXAMPLES 23 TO 42, AND COMPARATIVE APPLICATION EXAMPLES 15 TO 24

According to the same manner as that of Application Example 22 except that each of the flower thinning agents of Examples 2 to 21, and Comparative Examples 1 to 10 was used in place of the flower thinning agent of Example 1, an experiment was performed. Results are shown in Table 6 and Table 7.

COMPARATIVE APPLICATION EXAMPLE 25

According to the same manner as that of Application Example 22 except that a flower thinning agent containing a lime and sulfur agent as an effective ingredient was used in place of the flower thinning agent of Example 1, an experiment was performed. An effective ingredient concentration was based on a solid matter weight of a lime and sulfur agent. Results are shown in Table 7.

COMPARATIVE APPLICATION EXAMPLE 26

According to the same manner as that of Application Example 22 except that a flower thinning agent containing itaconic acid as an effective ingredient was used in place of the flower thinning agent of Example 1, an experiment was performed. An effective ingredient concentration was based on a solid matter weight of itaconic acid. Results are shown in Table 7.

COMPARATIVE APPLICATION EXAMPLE 27

According to the same manner as that of Application Example 22 except that a flower thinning agent containing high purity lecithin as an effective ingredient was used in place of the flower thinning agent of Example 1, an experiment was performed. An effective ingredient concentration was based on a solid matter weight of high purity lecithin. Results are shown in Table 7.

COMPARATIVE APPLICATION EXAMPLE 28

According to the same manner as that of Application Example 22 except that water (control) was used in place of the flower thinning agent of Example 1, an experiment was performed. Results are shown in Table 7.

TABLE 6

| | Flower thinning agent used | Effective ingredient conc. (%) | Remaining fruit rate (%) | medicine damage |
|---|---|---|---|---|
| Appln. Ex. 22 | Agent of Ex. 1 | 0.33 | 50.4 | ⊚ |
| | | 1.00 | 49.0 | ⊚ |
| Appln. Ex. 23 | Agent of Ex. 2 | 0.33 | 67.9 | ⊚ |
| | | 1.00 | 62.5 | ⊚ |
| Appln. Ex. 24 | Agent of Ex. 3 | 0.33 | 55.3 | ○ |
| | | 1.00 | 51.8 | □ |
| Appln. Ex. 25 | Agent of Ex. 4 | 0.33 | 39.8 | ⊚ |
| | | 1.00 | 38.9 | ⊚ |
| Appln. Ex. 26 | Agent of Ex. 5 | 0.33 | 55.5 | ⊚ |
| | | 1.00 | 52.3 | ⊚ |
| Appln. Ex. 27 | Agent of Ex. 6 | 0.33 | 50.5 | ⊚ |
| | | 1.00 | 47.7 | ⊚ |
| Appln. Ex. 28 | Agent of Ex. 7 | 0.33 | 38.6 | ⊚ |
| | | 1.00 | 35.8 | ⊚ |
| Appln. Ex. 29 | Agent of Ex. 8 | 0.33 | 44.3 | ⊚ |
| | | 1.00 | 39.9 | ⊚ |
| Appln. Ex. 30 | Agent of Ex. 9 | 0.33 | 65.5 | ⊚ |
| | | 1.00 | 60.9 | ⊚ |
| Appln. Ex. 31 | Agent of Ex. 10 | 0.33 | 55.3 | ⊚ |
| | | 1.00 | 51.7 | ⊚ |
| Appln. Ex. 32 | Agent of Ex. 11 | 0.33 | 44.3 | ⊚ |
| | | 1.00 | 42.5 | ○ |
| Appln. Ex. 33 | Agent of Ex. 12 | 0.33 | 56.9 | ⊚ |
| | | 1.00 | 52.2 | ⊚ |
| Appln. Ex. 34 | Agent of Ex. 13 | 0.33 | 51.2 | □ |
| | | 1.00 | 49.1 | □ |

TABLE 6-continued

| | Flower thinning agent used | Effective ingredient conc. (%) | Remaining fruit rate (%) | medicine damage |
|---|---|---|---|---|
| Appln. Ex. 35 | Agent of Ex. 14 | 0.33 | 48.2 | ⊚ |
| | | 1.00 | 44.8 | ⊚ |
| Appln. Ex. 36 | Agent of Ex. 15 | 0.33 | 49.1 | ⊚ |
| | | 1.00 | 47.8 | ⊚ |
| Appln. Ex. 37 | Agent of Ex. 16 | 0.33 | 48.2 | ○ |
| | | 1.00 | 46.5 | ○ |
| Appln. Ex. 38 | Agent of Ex. 17 | 0.33 | 57.1 | ⊚ |
| | | 1.00 | 53.9 | ○ |
| Appln. Ex. 39 | Agent of Ex. 18 | 0.33 | 54.1 | ⊚ |
| | | 1.00 | 50.6 | ⊚ |
| Appln. Ex. 40 | Agent of Ex. 19 | 0.33 | 42.2 | ⊚ |
| | | 1.00 | 40.8 | ⊚ |
| Appln. Ex. 41 | Agent of Ex. 20 | 0.33 | 40.2 | ⊚ |
| | | 1.00 | 38.5 | ⊚ |
| Appln. Ex. 42 | Agent of Ex. 21 | 0.33 | 57.8 | ⊚ |
| | | 1.00 | 53.5 | ⊚ |

TABLE 7

| | Flower thinning agent used | Effective ingredient conc. (%) | Remaining fruit rate (%) | medicine damage |
|---|---|---|---|---|
| Comp. Appln. Ex. 15 | Agent of Comp. Ex. 1 | 0.33 | 70.3 | □ |
| | | 1.00 | 68.8 | Δ |
| Comp. Appln. Ex. 16 | Agent of Comp. Ex. 2 | 0.33 | 68.0 | Δ |
| | | 1.00 | 66.2 | Δ |
| Comp. Appln. Ex. 17 | Agent of Comp. Ex. 3 | 0.33 | 83.8 | ⊚ |
| | | 1.00 | 81.0 | ⊚ |
| Comp. Appln. Ex. 18 | Agent of Comp. Ex. 4 | 0.33 | 70.6 | Δ |
| | | 1.00 | 68.6 | Δ |
| Comp. Appln. Ex. 19 | Agent of Comp. Ex. 5 | 0.33 | 68.2 | Δ |
| | | 1.00 | 66.9 | Δ |
| Comp. Appln. Ex. 20 | Agent of Comp. Ex. 6 | 0.33 | 82.2 | ⊚ |
| | | 1.00 | 79.9 | ⊚ |
| Comp. Appln. Ex. 21 | Agent of Comp. Ex. 7 | 0.33 | 84.7 | ⊚ |
| | | 1.00 | 81.7 | ⊚ |
| Comp. Appln. Ex. 22 | Agent of Comp. Ex. 8 | 0.33 | 66.6 | Δ |
| | | 1.00 | 64.9 | Δ |
| Comp. Appln. Ex. 23 | Agent of Comp. Ex. 9 | 0.33 | 72.7 | Δ |
| | | 1.00 | 69.9 | Δ |
| Comp. Appln. Ex. 24 | Agent of Comp. Ex. 10 | 0.33 | 66.1 | Δ |
| | | 1.00 | 64.0 | Δ |
| Comp. Appln. Ex. 25 | Agent containing a lime sulfur | 0.33 | 57.1 | Δ |
| | | 1.00 | 50.1 | Δ |
| Comp. Appln. Ex. 26 | Agent containing itaconic acid | 0.33 | 57.9 | Δ |
| | | 1.00 | 53.3 | X |
| Comp. Appln. Ex. 27 | Agent containing high purity lecithin | 0.15 | 72.9 | Δ |
| | | 0.45 | 67.3 | Δ |
| Comp. Appln. Ex. 28 | Water (control) | — | 90.1 | ⊚ |

APPLICATION EXAMPLE 43

Using a grape (King Dela) tree, flower thinning effect was confirmed. That is, using the aforementioned grape tree, the flower thinning agent of Example 1 was spread at a concentration indicated in Table 8 two times, at a flowering rate of 30% and 80%. An effective ingredient concentration was based on a solid matter weight of an inorganic compound of poor water solubility. Treatment was every branch treatment, and the agent was spread with a back loading sprayer.

Assessment was expressed as a remaining fruit rate regarding the number of flowering. Regarding medicine damage, results of observation of a leaf state such as defoliation, discolored leaf and deformed leaf were expressed by the following five stages. Results are shown in Table 8.

⊚: Normal
○: Extremely small damage
□: Small damage
Δ: Intermediate damage
×: Great damage

APPLICATION EXAMPLES 44 TO 63, AND COMPARATIVE APPLICATION EXAMPLES 29 TO 38

According to the same manner as that of Application Example 43 except that any of the flower thinning agents of Examples 2 to 21, and Comparative Examples 1 to 10 was used in place of the flower thinning agent of Example 1, an experiment was performed. Results are shown in Table 8 and Table 9.

COMPARATIVE APPLICATION EXAMPLE 39

According to the same manner as that of Application Example 43 except that a flower thinning agent containing a lime and sulfur mixture as an effective ingredient was used in place of the flower thinning agent of Example 1, an experiment was performed. An effective ingredient concentration was based on a solid matter weight of a lime and sulfur mixture. Results are shown in Table 9.

COMPARATIVE APPLICATION EXAMPLE 40

According to the same manner as that of Application Example 43 except that the flower thinning agent containing itaconic acid as an effective ingredient was used in place of the flower thinning agent of Example 1, an experiment was performed. An effective ingredient concentration was based on a solid matter weight of itaconic acid. Results are shown in Table 9.

COMPARATIVE APPLICATION EXAMPLE 41

According to the same manner as that of Application Example 43 except that a flower thinning agent containing high purity lecithin as an effective ingredient was used in place of the flower thinning agent of Example 1, an experiment was performed. An effective ingredient concentration was based on a solid matter weight of high purity lecithin. Results are shown in Table 9.

COMPARATIVE APPLICATION EXAMPLE 42

According to the same manner as that of Application Example 43 except that water (control) was used in place of the flower thinning agent of Example 1, and an experiment was performed. Results are shown in Table 9.

TABLE 8

| | Flower thinning agent used | Effective ingredient conc. (%) | Remaining fruit rate (%) | medicine damage |
|---|---|---|---|---|
| Appln. Ex. 43 | Agent of Ex. 1 | 0.33 | 50.2 | ⊚ |
| | | 1.00 | 46.2 | ⊚ |
| Appln. Ex. 44 | Agent of Ex. 2 | 0.33 | 65.9 | ⊚ |
| | | 1.00 | 63.4 | ⊚ |
| Appln. Ex. 45 | Agent of Ex. 3 | 0.33 | 55.4 | ○ |
| | | 1.00 | 51.6 | □ |
| Appln. Ex. 46 | Agent of Ex. 4 | 0.33 | 39.5 | ⊚ |
| | | 1.00 | 38.0 | ⊚ |

TABLE 8-continued

| | Flower thinning agent used | Effective ingredient conc. (%) | Remaining fruit rate (%) | medicine damage |
|---|---|---|---|---|
| Appln. Ex. 47 | Agent of Ex. 5 | 0.33 | 56.5 | ◎ |
| | | 1.00 | 52.0 | ◎ |
| Appln. Ex. 48 | Agent of Ex. 6 | 0.33 | 49.9 | ◎ |
| | | 1.00 | 45.3 | ◎ |
| Appln. Ex. 49 | Agent of Ex. 7 | 0.33 | 38.5 | ◎ |
| | | 1.00 | 35.1 | ◎ |
| Appln. Ex. 50 | Agent of Ex. 8 | 0.33 | 44.8 | ◎ |
| | | 1.00 | 39.5 | ◎ |
| Appln. Ex. 51 | Agent of Ex. 9 | 0.33 | 65.9 | ◎ |
| | | 1.00 | 60.5 | ◎ |
| Appln. Ex. 52 | Agent of Ex. 10 | 0.33 | 55.5 | ◎ |
| | | 1.00 | 51.3 | ◎ |
| Appln. Ex. 53 | Agent of Ex. 11 | 0.33 | 43.8 | ◎ |
| | | 1.00 | 41.5 | ○ |
| Appln. Ex. 54 | Agent of Ex. 12 | 0.33 | 55.8 | ◎ |
| | | 1.00 | 52.1 | ◎ |
| Appln. Ex. 55 | Agent of Ex. 13 | 0.33 | 51.9 | □ |
| | | 1.00 | 49.8 | □ |
| Appln. Ex. 56 | Agent of Ex. 14 | 0.33 | 48.9 | ◎ |
| | | 1.00 | 46.2 | ◎ |
| Appln. Ex. 57 | Agent of Ex. 15 | 0.33 | 49.9 | ◎ |
| | | 1.00 | 45.5 | ◎ |
| Appln. Ex. 58 | Agent of Ex. 16 | 0.33 | 48.0 | ○ |
| | | 1.00 | 46.1 | ○ |
| Appln. Ex. 59 | Agent of Ex. 17 | 0.33 | 55.1 | ◎ |
| | | 1.00 | 52.1 | ○ |
| Appln. Ex. 60 | Agent of Ex. 18 | 0.33 | 54.8 | ◎ |
| | | 1.00 | 50.2 | ◎ |
| Appln. Ex. 61 | Agent of Ex. 19 | 0.33 | 43.9 | ◎ |
| | | 1.00 | 41.8 | ◎ |
| Appln. Ex. 62 | Agent of Ex. 20 | 0.33 | 38.3 | ◎ |
| | | 1.00 | 35.8 | ◎ |
| Appln. Ex. 63 | Agent of Ex. 21 | 0.33 | 56.8 | ◎ |
| | | 1.00 | 53.8 | ◎ |

TABLE 9

| | Flower thinning agent used | Effective ingredient conc. (%) | Remaining fruit rate (%) | medicine damage |
|---|---|---|---|---|
| Comp. Appln. Ex. 29 | Agent of Comp. Ex. 1 | 0.33 | 71.3 | □ |
| | | 1.00 | 68.9 | Δ |
| Comp. Appln. Ex. 30 | Agent of Comp. Ex. 2 | 0.33 | 68.0 | Δ |
| | | 1.00 | 66.2 | Δ |
| Comp. Appln. Ex. 31 | Agent of Comp. Ex. 3 | 0.33 | 83.5 | ◎ |
| | | 1.00 | 81.5 | ◎ |
| Comp. Appln. Ex. 32 | Agent of Comp. Ex. 4 | 0.33 | 70.1 | Δ |
| | | 1.00 | 68.9 | Δ |
| Comp. Appln. Ex. 33 | Agent of Comp. Ex. 5 | 0.33 | 68.2 | Δ |
| | | 1.00 | 66.5 | Δ |
| Comp. Appln. Ex. 34 | Agent of Comp. Ex. 6 | 0.33 | 82.2 | ◎ |
| | | 1.00 | 79.5 | ◎ |
| Comp. Appln. Ex. 35 | Agent of Comp. Ex. 7 | 0.33 | 84.2 | ◎ |
| | | 1.00 | 81.2 | ◎ |
| Comp. Appln. Ex. 36 | Agent of Comp. Ex. 8 | 0.33 | 66.6 | Δ |
| | | 1.00 | 64.5 | Δ |
| Comp. Appln. Ex. 37 | Agent of Comp. Ex. 9 | 0.33 | 73.7 | Δ |
| | | 1.00 | 69.9 | Δ |
| Comp. Appln. Ex. 38 | Agent of Comp. Ex. 10 | 0.33 | 67.2 | Δ |
| | | 1.00 | 64.5 | Δ |
| Comp. Appln. Ex. 39 | Agent containing a lime sulfur | 0.33 | 57.5 | Δ |
| | | 1.00 | 50.5 | Δ |
| Comp. Appln. Ex. 40 | Agent containing itaconic acid | 0.33 | 57.5 | Δ |
| | | 1.00 | 53.0 | X |
| Comp. Appln. Ex. 41 | Agent containing high purity lecithin | 0.15 | 72.5 | Δ |
| | | 0.45 | 67.0 | Δ |
| Comp. Appln. Ex. 42 | Water (control) | — | 91.2 | ◎ |

APPLICATION EXAMPLE 64

Using a pear (Kosui) tree, flower thinning effect was confirmed. That is, using the aforementioned pear tree, the flower thinning agent of Example 1 was spread at a concentration indicated in Table 10 two times, at a flowering rate of 30% and 80%. In this respect, at the present experiment, an air temperature at flowering was low, and weather was bad. Therefore, a scatter in flowering was greater than usual. An effective ingredient concentration was based on a solid matter weight of an inorganic compound of poor water solubility. Treatment was every branch treatment, and the agent was spread with a back loading sprayer.

Assessment was expressed as a remaining fruit rate relative to the number of flowering. Regarding medicine damage, results of observation of a leaf state such as defoliation, discolored leaf and deformed leaf were expressed by the following five stages. Results are shown in Table 9.

: Normal
○: Extremely small damage
□: Small damage
Δ: Intermediate damage
×: Great damage

APPLICATION EXAMPLES 65 TO 70, AND COMPARATIVE APPLICATION EXAMPLES 43 TO 46

According to the same manner as that of Application Example 64 except that any of the flower thinning agents of Examples 4, 5, 7, 9, 15 and 21, and Comparative Examples 1, 4, 8 and 10 was used in place of the flower thinning agent of Example 1, an experiment was performed. Results are shown in Table 10 and Table 11.

COMPARATIVE APPLICATION EXAMPLE 47

According to the same manner as that of Application Example 64 except that a flower thinning agent containing a lime and sulfur agent as an effective ingredient was used in place of the flower thinning agent of Example 1, an experiment was performed. An effective ingredient concentration was based on a solid matter weight of a lime and sulfur agent. Results are shown in Table 11.

COMPARATIVE APPLICATION EXAMPLE 48

According to the same manner as that of Application Example 64 except that a flower thinning agent containing itaconic acid as an effective ingredient was used in place of the flower thinning agent of Example 1, an experiment was performed. An effective ingredient concentration was based on a solid matter weight of itaconic acid. Results are shown in Table 11.

COMPARATIVE APPLICATION EXAMPLE 49

According to the same manner as that of Application Example 64 except that a flower thinning agent containing high purity lecithin as an effective ingredient was used in place of the flower thinning agent of Example 1, an experiment was performed. An effective ingredient concentration was based on a solid matter weight of high purity lecithin. Results are shown in Table 11.

COMPARATIVE APPLICATION EXAMPLE 50

According to the same manner as that of Application Example 64 except that a flower thinning agent containing calcium formate as an effective ingredient was used in place of the flower thinning agent of Example 1, an experiment was performed. An effective ingredient concentration was based on a solid matter weight of calcium formate. Results are shown in Table 11.

COMPARATIVE APPLICATION EXAMPLE 51

According to the same manner as that of Application Example 64 except that water (control) was used in place of the flower thinning agent of Example 1, an experiment was performed. Results are shown in Table 11.

TABLE 10

| | Flower thinning agent used | Effective ingredient conc. (%) | Remaining fruit rate (%) | medicine damage |
|---|---|---|---|---|
| Appln. Ex. 64 | Agent of Ex. 1 | 0.33 | 54.5 | ◎ |
| | | 1.00 | 51.9 | ◎ |
| Appln. Ex. 65 | Agent of Ex. 4 | 0.33 | 42.2 | ◎ |
| | | 1.00 | 38.9 | ◎ |
| Appln. Ex. 66 | Agent of Ex. 5 | 0.33 | 58.6 | ◎ |
| | | 1.00 | 55.0 | ◎ |
| Appln. Ex. 67 | Agent of Ex. 7 | 0.33 | 39.6 | ◎ |
| | | 1.00 | 36.2 | ◎ |
| Appln. Ex. 68 | Agent of Ex. 9 | 0.33 | 66.8 | ◎ |
| | | 1.00 | 61.8 | ◎ |
| Appln. Ex. 69 | Agent of Ex. 15 | 0.33 | 53.2 | ◎ |
| | | 1.00 | 49.7 | ◎ |
| Appln. Ex. 70 | Agent of Ex. 21 | 0.33 | 57.0 | ◎ |
| | | 1.00 | 52.6 | ◎ |

TABLE 11

| | Flower thinning agent used | Effective ingredient conc. (%) | Remaining fruit rate (%) Lateral flower | medicine damage |
|---|---|---|---|---|
| Comp. Appln. Ex. 43 | Agent of Comp. Ex. 1 | 0.33 | 76.3 | □ |
| | | 1.00 | 74.4 | Δ |
| Comp. Appln. Ex. 44 | Agent of Comp. Ex. 4 | 0.33 | 76.2 | □ |
| | | 1.00 | 74.6 | Δ |
| Comp. Appln. Ex. 45 | Agent of Comp. Ex. 8 | 0.33 | 72.6 | Δ |
| | | 1.00 | 70.9 | Δ |
| Comp. Appln. Ex. 46 | Agent of Comp. Ex. 10 | 0.33 | 71.9 | Δ |
| | | 1.00 | 69.0 | Δ |
| Comp. Appln. Ex. 47 | Agent containing a lime sulfur | 0.33 | 65.1 | Δ |
| | | 1.00 | 60.1 | Δ |
| Comp. Appln. Ex. 48 | Agent containing itaconic acid | 0.33 | 70.0 | Δ |
| | | 1.00 | 63.9 | X |
| Comp. Appln. Ex. 49 | Agent containing high purity lecithin | 0.15 | 80.1 | □ |
| | | 0.45 | 73.1 | Δ |
| Comp. Appln. Ex. 50 | calcium formate | 0.15 | 79.9 | □ |
| | | 0.45 | 72.3 | Δ |
| Comp. Appln. Ex. 51 | Water (control) | — | 91.7 | ◎ |

As shown in the aforementioned Table 4 to Table 11, the flower thinning agents of the present invention used in Application Examples 1 to 70 exhibited appropriate flower thinning effect and, at the same time, caused little medicine damage.

On the other hand, the flower thinning agent used in Comparative Application Example 3 became delayed-acting due to too great BET specific surface area of an inorganic compound of poor water solubility, and had insufficient flower thinning effect. In addition, in the flower thinning agents of Comparative Application Examples 11 to 13, occurrence of remarkable medicine damage was recognized. Further, as shown in Tables 10 and 11, in the flower thinning agents used in Comparative Application Examples 47 to 50, which contain the known flower thinning agent, flower thinning effect was remarkably reduced as compared with the normal weather, while the flower thinning agent of the present invention can exert certain flower thinning effect even when weather is bad.

INDUSTRIAL APPLICABILITY

As described above, the flower thinning agent of the present invention is not harmful to a human body, friendly to the environment, and has high flower thinning effect. In addition, since the flower thinning agent of the present invention is also excellent in sustained release effect, a freedom degree of spread term is widened than usual, and handling is also excellent.

The invention claimed is:

1. A particulate flower thinning agent which comprises a preparation of a mixture of an inorganic compound of poor water solubility with an additive, the inorganic compound being at least one kind selected from silica, calcium carbonate, zeolite, magnesium phosphate, and magnesium carbonate, and the additive being at least one kind selected from condensed phosphoric acid and a salt thereof, lecithin, sterol, amino acid, and sucrose fatty acid ester, wherein the particulate flower thinning agent satisfies the following relationships of (a), (b) and (c):

$$1.2 \leq P \leq 30 \qquad (a)$$

$$3 \leq Q \leq 800 \qquad (b)$$

$$0.5 \leq Q/P \leq 1000 \qquad (c)$$

P: average particle diameter (μm) measured by SALD-2000A laser type particle size distribution meter Q: BET specific surface area (m$^2$/g) measured according to the nitrogen adsorption method.

2. The particulate flower thinning agent of claim 1, wherein the particulate flower thinning agent satisfies the following relationships (d), (e) and (f):

$$1.2 \leq P \leq 10 \qquad (d)$$

$$7 \leq Q \leq 300 \qquad (e)$$

$$0.5 \leq Q/P \leq 300 \qquad (f).$$

3. The particulate flower thinning agent of claim 1, wherein the particulate flower thinning agent satisfies the following relationships (g), (h) and (i):

$$1.2 \leq P \leq 5 \quad (g)$$

$$10 \leq Q \leq 200 \quad (h)$$

$$1 \leq Q/P \leq 150 \quad (i).$$

4. A particulate flower thinning agent according to any one of claims 1 to 3, wherein the inorganic compound of poor water solubility is at least one kind selected from silicate mineral, zeolite, and magnesium phosphate.

5. A particulate flower thinning agent which comprises a mixture comprising calcium phosphate and an additive, the additive being at least one kind selected from condensed phosphoric acid and a salt thereof, lecithin, sterol, amino acid, and sucrose fatty acid ester, wherein the particulate flower thinning agent satisfies the following relationships of (a), (e), (m) and (n):

$$1.2 \leq P \leq 30 \quad (a)$$

$$3 \leq Q \leq 300 \quad (e)$$

$$0.01 \leq R \leq 30 \quad (m)$$

$$0.5 \leq S \leq 300 \quad (n)$$

P: average particle diameter (μm) measured by SALD-2000A laser type particle size distribution meter Q: BET specific surface area (m²/g) measured according to the nitrogen adsorption method R: average particle diameter (μm) of particles measured by electron micrograph S= BET specific surface area Q (m²/g) measured according to the nitrogen adsorption method/specific surface area Q1 (m²/g) calculated from average particle diameter R of particles measured by electron micrograph.

6. A particulate flower thinning agent which comprises a mixture comprising calcium phosphate and an additive, the additive being at least one kind selected from condensed phosphoric acid and a salt thereof, lecithin, sterol, amino acid, and sucrose fatty acid ester, wherein the particulate flower thinning agent satisfies the following relationships of (a), (e), (o) and (t):

$$1.2 \leq P \leq 30 \quad (a)$$

$$3 \leq Q \leq 300 \quad (e)$$

$$0.01 \leq R \leq 10 \quad (o)$$

$$0.5 \leq S \leq 100 \quad (t)$$

P: average particle diameter (μm) measured by SALD-2000A laser type particle size distribution meter Q: BET specific surface area (m²/g) measured according to the nitrogen adsorption method R: average particle diameter (μm) of particles measured by electron micrograph S= BET specific surface area Q (m²/g) measured according to the nitrogen adsorption method/specific surface area Q1 (m²/g) calculated from average particle diameter R of particles measured by electron micrograph.

7. A particulate flower thinning agent which comprises a mixture comprising calcium phosphate and an additive, the additive being at least one kind selected from condensed phosphoric acid and a salt thereof, lecithin, sterol, amino acid, and sucrose fatty acid ester, wherein the particulate flower thinning agent satisfies the following relationships of (a), (e), (u) and (v):

$$1.2 \leq P \leq 30 \quad (a)$$

$$3 \leq Q \leq 300 \quad (e)$$

$$0.01 \leq R \leq 5 \quad (u)$$

$$0.5 < S \leq 10 \quad (v)$$

P: average particle diameter (μm) measured by SALD-2000A laser type particle size distribution meter Q: BET specific surface area (m²/g) measured according to the nitrogen adsorption method R: average particle diameter (μm) of particles measured by electron micrograph S= BET specific surface area Q (m²/g) measured according to the nitrogen adsorption method/specific surface area Q1 (m²/g) calculated from average particle diameter R of particles measured by electron micrograph.

8. A particulate flower thinning agent according to any one of claims 1-3 and 5-7, wherein an amount of the additive is 0.005 to 200 parts by weight per 100 parts by weight of the inorganic compound of poor water solubility.

* * * * *